US005716611A

United States Patent [19]
Oshlack et al.

[11] Patent Number: 5,716,611
[45] Date of Patent: Feb. 10, 1998

[54] EMOLLIENT ANTIMICROBIAL FORMULATIONS CONTAINING POVIDONE IODINE

[75] Inventors: Benjamin Oshlack, New York, N.Y.; Mark Chasin, Manalapan, N.J.; Richard Sackler, Greenwich, Conn.; Dileep Bhagwat, Bronxville, N.Y.

[73] Assignee: Euro-Celtique, S.A., Luxembourg, Luxembourg

[21] Appl. No.: 582,851

[22] Filed: Jan. 2, 1996

[51] Int. Cl.⁶ .......................... A61K 31/79; A61K 31/50
[52] U.S. Cl. ...................... 424/78.25; 424/78.07; 424/78.02
[58] Field of Search .................... 424/78.02, 78.25

[56] References Cited

U.S. PATENT DOCUMENTS

| | | | |
|---|---|---|---|
| 2,739,922 | 3/1956 | Shelanski | 524/548 |
| 4,478,853 | 10/1984 | Chausee | 424/358 |
| 4,725,433 | 2/1988 | Matravers | 514/938 |
| 5,384,334 | 1/1995 | Polovsky et al. | 514/777 |
| 5,554,361 | 9/1996 | Dixon | 424/70.15 |

*Primary Examiner*—Peter F. Kulkosky
*Attorney, Agent, or Firm*—Steinberg, Raskin & Davidson, P.C.

[57] ABSTRACT

Novel topical formulations an anti-microbially effective amount of povidone iodine and a water-washable emollient, as well as, methods for their preparation, are disclosed.

19 Claims, No Drawings

EMOLLIENT ANTIMICROBIAL FORMULATIONS CONTAINING POVIDONE IODINE

BACKGROUND OF THE INVENTION

In the medical setting, it is necessary to maintain a substantially sterile environment. To this end, antimicrobial formulations are widely used to prevent transmission of disease causing agents, e.g. microbes, from individuals, particularly health care personnel who routinely contact patients, to other individuals, especially patients, who are more prone to infections due to their incapacitated state.

One method of maintaining an aseptic environment calls for routine cleansing and disinfecting of the environment, medical and surgical devices, etc. Because health care professionals routinely come in contact with patients, personal hygiene is a primary concern. To prevent the spread of disease from medical professional to the numerous patients who they come in contact with during the course of their professional duties, it is particularly important that the skin of those individuals, especially of the hands and arms, be thoroughly cleansed prior to contact with any patient.

Various antimicrobial or germicidal preparations are commercially available for use as antimicrobial scrubs, washes, or cleansers. Exemplary products include chlorhexidine gluconate (Hibiclens®, commercially available from Stuart Pharmaceuticals); hexachlorophene containing products such as cleansing emulsions and foams; alcohols such as ethyl and isopropyl alcohol; and benzalkonium chloride solution, tinctures, sprays, and towelettes (Zephiran®, commercially available from Winthrop Pharmaceuticals).

Although many compounds have antimicrobial properties, very few compounds are effective across a continuous spectrum of microbes. For example, hexachlorophene is primarily effective against gram-positive organisms while cationic antiseptics, e.g benzalkonium chloride, are not effective against sporulating organisms. In fact, some gram-negative bacteria, e.g. *Pseudomonas cepacia*, grow in solutions of benzalkonium chloride and thus may be responsible for outbreaks of hospital infections. Other bacteria are capable of growing in 70% ethanol solutions.

Certain antiseptics, e.g. iodine, have a broad range of anti-microbial activity. Iodine is particularly useful because it is active against bacteria, fungi, yeasts, protozoa, and viruses. A 1:20,000 iodine solution has been demonstrated to kill most bacteria within one minute. On the skin, a 1% iodine tincture will kill 90% of the bacteria in 90 seconds.

Povidone-Iodine (PVPI) is a particularly useful antimicrobial preparation which contains iodine as its active agent. PVPI is a complex of iodine with povidone.

Because the available iodine in PVPI which provides the antiseptic activity, PVPI is effective against a broad spectrum of microbes. PVPI provides a longer period of antimicrobial activity than other iodine products, e.g. iodine tincture. Studies have demonstrated that it takes six to eight hours for the skin bacterial population to return to normal after treatment with a 10% povidone iodine solution.

PVPI containing products have been widely used as safe and effective antimicrobials since the late 1950's when it was first discovered by Shelanski (U.S. Pat. No. 2,739,922). Historically, iodophor solutions, particularly PVPI solutions have been recognized as safe and effective microbicidals. Solutions of PVPI are known to be inherently unstable but can be stabilized by the addition of other stabilizers or iodine donating species such as iodate salts as disclosed in U.S. Pat. No. 4,113,857 (Shetty) and the use of iodide salts as disclosed in U.S. Pat. No. 4,996,048 (Bhagwat et al.), both of which are assigned to the Assignee of the present invention and hereby incorporated by reference. For dilute PVPI solutions for ophthalmic use, stabilization of the solution can be achieved by a suitable alkalizing agent and not buffering the solution as disclosed in U.S. Pat. No. 5,126,127 (Bhagwat et al.), assigned to the Assignee of the present invention and hereby incorporated by reference.

Many anti-microbial formulations intended for topical use, including PVPI solutions, contain surface active agents (surfactants). Surfactants used in anti-microbial containing aqueous formulations are water-soluble and are generally anionic, non-ionic or amphoteric in nature. The surfactant is added to the formulation in order to lower the surface tension of the product, which allows easier penetration and better contact of the product with the skin. It also provides the foam which aids in the cleaning process.

Normal human skin has a protective layer of fats and oils. This provides emolliency and prevents water loss. An undesirable side-effect of surfactants is that, upon application to the skin, they remove the natural layer of protective oils and fats by emulsification. The exposed skin is subject to water loss, causing chapping and irritation.

Irritation is a common complaint from health care personnel, particularly those who work hospital settings such as the operating room where frequent and repeated scrubbing of hands with an antimicrobial scrub (e.g. PVPI Scrub) is essential. Repeated and frequent use of antimicrobial or other topical products containing surfactants compounds the problem because there is insufficient time for the body to replace natural protective oils and fats removed by the surfactant. Further, skin stripped of its natural oils and fats is vulnerable to irritation from the anti-microbials themselves.

Emollients may be added to surfactant-containing pharmaceutical preparations in order to counter the drying and chapping effect of the surfactant(s). Many emollient agents are fat or oil based and, therefore, difficult to incorporate into aqueous solutions. Additionally, fats and oils contain unsaturated bonds which can react with an anti-microbial agent, such as the iodine present in a PVPI preparation, rendering the formulations both ineffective and unstable.

When these fats are part of an aqueous based formulation, they are generally emulsified and form a water insoluble second phase. Products containing fats are generally not rinsed off the skin.

Fats can be made water-soluble by incorporation of a polyoxyethylene hydrophilic chain into the fat molecular structure. These water-soluble compounds can be incorporated in aqueous anti-microbial formulations, e.g. solutions, dispersions and the like, to yield one aqueous phase. There is a great advantage in processing such a formulation as incorporation of water-washable fat simply involves dissolving this ingredient in water.

Water-washable fats are particularly useful as water-soluble emollients in pharmaceutical formulations because they can easily be incorporated into aqueous preparations. Water-soluble fats are generally effective as emollients when incorporated into topically applied products intended to stay on the skin (e.g., hand creams, lotions, etc.). Typically water-soluble emollients are present in such formulations in amounts of from 1–2%. To provide a desirable emollient effect, water-washable fats are generally incorporated into a formulation with other types of emollients, e.g. water-insoluble fats).

Water-soluble fats are not generally considered for use in aqueous formulations that are readily washed off the skin upon exposure to an aqueous environment, e.g. during washing or rinsing. Thus, because water-soluble emollients are not retained on the skin after washing, they are not particularly effective emollients when used in aqueous formulations which are not designed to remain in contact with the skin.

Additionally, because many water-soluble emollients contain a fatty/oily component, these molecules contain some degree of unsaturation (double bonds) in their molecule thereby having the potential to chemically react with other formulation ingredients, e.g. iodine, causing stability problems with the product. Thus, incorporation of a water-soluble emollient into an aqueous antimicrobial formulation, e.g. a PVPI formulation, inherently presents a formulator with numerous manufacturing and stability problems.

Thus, there is a need in the art for an emollient antimicrobial formulation which exhibits a broad spectrum of antiseptic, anti-protozoal, anti-fungal, antiviral, antimicrobial, disinfectant, anti-mycotic, and/or germicidal (collectively defined as anti-microbial or microbicidal for purposes of the present invention) activity which at the same time alleviates dryness and chapping of skin upon repeated use. The product is preferably stable for a pharmaceutically acceptable period of time, e.g. at least about one year, and most two years or longer.

OBJECTS AND SUMMARY OF THE INVENTION

It is therefore an object of the present invention to provide pharmaceutically acceptable anti-microbial preparations which incorporate at least one water-soluble emollient to alleviate drying of the skin.

It is another object of the present invention to provide a stable microbicidal aqueous solution of an iodophor, preferably PVPI, and a water-soluble emollient at a critical minimum concentration to significantly minimize the drying, total water loss and irritation of the skin, even on repeated and frequent use.

It is a further object of the present invention to provide a novel stable anti-microbial aqueous PVPI solution with emollient properties which is stable for two years or more in substantially non permeable pharmaceutical containers according to USP or FDA guidelines (e.g., high density polyethylene, glass).

It is a further object of the present invention to provide a process for preparing a PVPI solution which is effective as a microbicidal, minimizes the drying, total water loss and irritation of the skin upon repeated frequent use and is stable for at least 2 years as per the USP or FDA standards.

These objects and others are achieved by the present invention, which relates in part to a pharmaceutical formulation including an effective amount of iodophor to provide an antimicrobial effect and an effective amount of a water-soluble emollient which preferably comprises ethoxylated higher aliphatic alcohols such as ceteth-24, a cetostearyl alcohol compound reacted with a 24 mole adduct of ethylene oxide and/or an ethoxylated cholesterol derivative, e.g. choleth-24, an ethoxylated cholesterol fatty alcohol complex, to provide the formulation with surprisingly less irritating properties when applied to humam skin than a comparative formulation which does not include the aforementioned water-soluble emollient. This surprising effect is particularly apparent when the iodophor formulation includes greater than 2% water-soluble emollient. Preferably the water-soluble emollient component comprises from about 1 to about 99% of an ethoxylated higher aliphatic alcohol and/or from about 1 to about 99% of an ethoxylated cholesterol derivative. A combination of ceteth-24 and choleth-24 is commercially available as Solulan C-24® from Amerchol.

Another aspect of the present invention is directed to a method for preparing an antiseptic formulation comprising the step of combining povidone iodine with a water-soluble emollient including from about 1 to about 99% of an ethoxylated higher aliphatic alcohol and from about 1 to about 99% of an ethoxylated cholesterol derivative.

Yet another aspect of this invention is directed to a method of degerming skin by applying an effective amount a preparation of an anti-microbial and a water-soluble emollient to the skin of a mammal, particularly to the skin of a human.

The present invention is further related to an effective microbicidal scrub formulation comprising PVPI and a water-soluble emollient including from about 1 to about 99% of an ethoxylated higher aliphatic alcohol and from about 1 to about 99% of an ethoxylated cholesterol derivative, which surprisingly is significantly less irritating to the human skin, causes less erythema and reduced Total Water Loss (TWL) from the human skin as compared to the PVPI scrub without the water-soluble emollient.

DETAILED DESCRIPTION

All percentages disclosed herein are % weight ingredient/volume of final formulation unless otherwise indicated.

Iodophors

Combination of elemental iodine and certain organic polymers, e.g., polyvinylpyrrolidone and detergent polymers, have been termed iodophors. The organic polymers used to form an iodophor comprise a broad range in molecular weight and chain length, and may be either ionic or non-ionic in character, as well as possessing either surfactant or non-surfactant properties. A loose bond forms between the iodine and organic polymer to form a complex. Aqueous solutions of up to about 30% in iodine content, may be prepared.

The general method for the preparation of a iodophor complex is to bring into intimate contact, elemental diatomic iodine with the selected polymer, either in the dry or powder form or in the presence of a suitable solvent. Heat may be used to accelerate complex formation. Upon completion of the reaction, the iodophor complex of the respective polymeric carrier with iodine is obtained in certain reproducible proportions of one to the other.

Iodophor preparations are described in terms of available or titratable iodine which is considered to be the iodine released from the complex to exert germicidal action thereof. However, such available iodine determinations do not reflect either the total iodine content of the iodophor, or its germicidal potency. The iodine moiety of polyvinylpyrrolidone (povidone)-iodine complex is present in an aqueous iodophor solution in the form of different thermodynamically stable anionic iodine species and diatomic iodine. The anionic iodine forms are capable of generating diatomic iodine in the course of their respective equilibrium reactions. The anionic species do not distribute themselves into an extracting solvent which removes only the nonionic iodine. Such iodine is generated in the course of the iodine equilibrium reaction and extraction thereof by a solvent fractionates the equilibrium state. The disturbed equilibrium reaction is soon re-established to restore new anionic iodine species, but now at a different concentration level since the previous aqueous iodine content of the solution has been reduced by the extracting solvent.

Since the iodophor iodine exerting microbicidal action exists in solution in dynamic equilibrium with ionic iodine species, removal of one or more of the iodine species results in formation of new equilibrium forms. An extracting solvent removes or consumes iodine from the iodophor solution in a manner similar to that of a microbial and organic load during degerming use of the iodophor solution. The amount of iodine available for germicidal action is an iodophor preparation therefore is the amount of iodine in equilibrium in the solvent at the time of use. Such equilibrium iodine content represents the germicidal potency of the preparation, but not the total iodine content titrated for the preparation nor the apparent distribution of the iodine forms. Although iodophor solutions have been assayed in the art for available or titratable iodine, it is the equilibrium iodine which is the particular form of iodine present in the iodophor solution that is instantly available to exert microbicidal action. This form of iodine differs from titratable iodine and the other iodine species present in the iodophor solution. Therefore, the equilibrium iodine content of an iodophor solution is to be distinguished from its titratable iodine content.

The titratable iodine content of an iodophor preparation includes the iodine reservoir of the iodophor preparation (povidone iodine), as well as the equilibrium iodine in solution. Titratable iodine=Reservoir Iodine+Equilibrium Iodine However, it is the equilibrium iodine alone that exerts the microbicidal action of the preparation at any given moment. The portion of the titratable iodine content remaining after subtracting the amount of equilibrium iodine present, serves as the iodine reservoir to generate new equilibrium iodine in solution as it is consumed by the microbial and bio-organic load in the course of microbicidal activity, but does not exert such germicidal actin by itself.

Preferably the iodophors are present in amounts of from about 1 to about 30% w/v. When povidone iodine is the iodophor, it is preferably included in amounts of from about 2 to about 20% w/v of the formulation. PVPI is typically present in a range of from about 2 to about 10% w/v, and most preferably from about 5 to about 8% w/v.

Povidone-iodine (polyvinylpyrrolidone-iodine or PVPI) USP (U.S. Pharmacopeia) is the raw material used in the preparation of all PVPI containing formulations. Povidone-iodine is a complex of iodine with povidone. It contains not less than 9.0% by weight, and not more than 12% by weight of available-iodine (titratable iodine) calculated on a dry basis. Povidone Iodine USP has a specification for iodide ion of not more than 6.6% by weight on a dry basis. In certain preferred embodiments, the iodophor formulation contains more or less than the USP-specified amount of available-iodine. In certain formulations, the iodophor formulation contains from about 12% to about 30% available-iodine. In other situations, the amount of available iodine may be, e.g., 1%.

The level of iodide ions inherently present in any PVPI formulation using PVPI raw material, therefore depends on the amount of iodide ion present in the raw material PVPI used. For example, on a theoretical basis, if the PVPI contains 6% by weight iodide ion, then a formulation containing 10% by weight of a PVPI would contain 0.6% by weight iodide ion. However, PVPI raw material containing a level of iodide ion greater than specifications of the U.S. Pharmacopeia, could also be used in formulating a PVPI containing product.

Thus, the minimum amount of iodide ion inherently present in a PVPI formulation could he as low as 0.0% by weight, while the maximum amount of iodide ion inherently present in such a PVPI formulation would be the amount contributed by the PVPI raw material used to formulate the same. For example, on a theoretical basis, if a formulation contains 0.36% by weight PVPI, and the PVPI contains the maximum iodide allowable of 6.6% by weight, then the formulation will have 0.0237% by weight iodide present.

Water-Soluble Emollients

It is known in the art that water-soluble or water-washable fats (hereinafter used interchangeably) are generally used in creams or lotions intended to remain on the skin. Because water-washable fats are soluble upon exposure to an aqueous environment, they are not generally considered for use in pharmaceutical preparations which are intended for use in or exposure to un aqueous environment because they will be removed from the skin upon exposure to that environment, thus lessening the desired emollient effect. Therefore, one skilled in the art would understand that the addition of an amount of water-soluble emollient beyond that used generally in such formulations would be wasteful, because it would be washed off the skin upon exposure to an aqueous environment.

It has been surprisingly discovered that the addition of a water-soluble emollient to a pharmaceutical antimicrobial formulation, e.g., a scrub, particularly in an amount in excess of that which would generally be used in the industry, e.g. 1–2%, provides a greater emollient effect than that obtained with the amount generally included in such preparations.

The novel formulations of the present invention include an iodophor and a particular water-soluble emollient comprising from about 1 to about 99% of an ethoxylated higher aliphatic alcohol and from about 1 to about 99% of an ethoxylated cholesterol derivative. The formulations of the present invention may optionally include at least one surfactant, as well as various pharmaceutical excipients, thickening agents, pH adjusters, vehicles, and the like.

One aspect of the invention concerns the novel incorporation of a water-soluble emollient comprising including from about 1 to about 99% of an ethoxylated higher aliphatic alcohol and from about 1 to about 99% of an ethoxylated cholesterol derivative in the formulation in an amount greater than that recommended by the manufacturer, which provides improved emollient properties and decreased side effects, e.g. irritation. For example, it is recommended by the manufacturer that Solulan C-24® be incorporated in amounts of about 1–2% of the final formulation. However, it has been surprisingly discovered that incorporation of Solulan C-24® in amounts greater than 2%, e.g. from greater than 2% to about 30% of the final formulation, yield improved emollient results as set forth in the Examples below. One skilled in the art will understand that more of the water-soluble emollient can be incorporated into the formulation (e.g., greater than 30% by weight), but that the benefit would not necessarily be approved because this excess would be washed off the skin.

Water-soluble emollients are incorporated to prevent adverse effects associated with repeated use of the antimicrobial preparations of the prior art. Preferably, the water-soluble emollients are water-washable compounds such as water-washable fats. A non-limiting list of suitable emollients which may be used in accordance with the present invention include ethoxylated higher aliphatic alcohol derivatives such as ceteth-24, a cetostearyl alcohol reacted with a 24 mole adduct of ethylene oxide, and ethoxylated cholesterol derivatives such as choleth-24. A preferred water-soluble emollient combination comprises from about 1 to about 99% of an ethoxylated higher aliphatic alcohol, e.g., choleth-24, and from about 1 to about 99% of an ethoxylated cholesterol derivatives, e.g., ceteth-24. Other water-soluble emollients which may also be used in accordance with the present invention and include polyethylene-6 glycerol—caprylate\caprate (commercially available as Softigen 767 from Hüls America); methyl gluceth-20, the 20 mole ethoxylate of methyl glucose (commercially available as Glucam E 20 from Amerchol), aloe powder, aloe liquid and the like.

The water-soluble emollients are present in the formulation in amounts ranging from about 0.1% to about 30% w/v. Particular benefits are achieved when the water-soluble emollients are present in amounts of greater than 2%, preferably from greater than 2 to about 30% w/v, and most preferably from greater than 2 to about 20% w/v.

Surfactants may also be included in the formulations of the present invention. There are many surfactants known in the art which may be used in accordance with the present invention, including amphoteric, anionic, cationic and non-ionic. A non-limiting list of surfactants which may be used in accordance with the present invention include long-alkyl-chain sulfonates, alkyl aryl sulfonates, dialkyl sodium sulfosuccinates, alkyl sulfates, quaternary ammonium salts, fatty alcohols such as lauryl, cetyl and stearyl alcohols; glyceryl esters such as mono-, di- and triglycerides; and fatty acid esters of fatty alcohols and other alcohols such as propylene glycol, polyethylene glycol, sorbitan, sucrose and cholesterol; polyoxyethylene glyceryl, steroidal esters, poly-oxypropylene esters, and combinations thereof.

It is well known in the pharmaceutical art that surfactants have many different properties and that a particular surfactant will provide its own unique properties. Surfactants are used as detergents, foam boosters, wetting agents, foaming agents, emulsifiers, emollients, and solubilizers among other uses. For a more complete discussion of surfactants and their properties, see Remington's Pharmaceutical Sciences, 17th edition, pp. 258–329 and Othmer, Encyclopedia of Chemical Technology, 3rd Edition, Volume 22, pages 332–432.

Surfactants used in accordance with the present invention generally include those compounds with superior foam boosting, detergent and emollient properties. Preferred surfactants for use with the present invention include ethanol amines reacted with fatty acids such as ammonium nonoxynol 4 sulfate, mixtures of ethanolamides of lauric acid such as lauramide DEA; and cocamidopropyl betaine, a zwitterion derived from fatty acids form coconut oil, commercially available as Velvetex BA 35® from Henkel.

Surfactants preferred for superior detergent properties include ethoxylated higher aliphatic alcohol derivatives such as phenol derivatives containing 3–4 moles of ethylene oxide. Preferably, the aliphatic alcohol moiety is attached to a phenol ring. A preferred ethoxylated higher aliphatic alcohol derivative is ammonium Nonoxynol-4 sulfate, the ammonium salt of sulfated Nonoxynol-4, commercially available as Rhodapex CO-436® from Rhône-Poulenc.

Surfactants useful for foam-boosting properties include ethanol amines reacted with fatty acids, commercially available as Superamide L9® from Onyx.

When surfactants are included in the present invention, they are generally present in a range from about 0.1 to about 30% w/v, and preferably from about 1.0 to about 28% w/v.

Stabilizers may be added to the inventive formulations in order to provide a desired shelf-life. The stabilizers promote product stability by a variety of mechanisms, including but not limited to anti-oxidant and anti-microbial mechanisms. When PVPI is present in the formulation, the stabilizer is preferably iodine or a salt thereof, an iodate salt or an iodide salt. A preferred stabilizer is potassium iodate. When potassium iodate is the stabilizer, it is present in an amount of from 0.01 to about 10% w/v of the final formulation. The amount of potassium iodate used is dependent on factors, including the amount of PVPI present in the formulation.

Thickening or viscosity agents may be added to the formulations to adjust the preparation to a desired viscosity. Any suitable viscosity agents may be used in accordance with the present invention. Preferred thickening agents include hydroxyethylcellulose commercially available as Natrosol 250 HX® from Aqualon and cellulose derivatives such as hydroxypropyl methylcellulose, commercially available as Methocel E 50® from Dow Chemical.

The viscosity agents are generally present from about 0.1 to about 30% w/v of the final formulation. One skilled in the art can achieve a desired viscosity by adding a viscosity agent or a combination of viscosity agents; such formulations are contemplated to be within the scope of the present invention.

The formulations of the present invention preferably include a pharmaceutically acceptable vehicle. Various vehicles can be used in accordance with the present invention. Preferably, the vehicle is an aqueous vehicle such as water or a water/alcoholic solution. The vehicle will be present in a sufficient amount to achieve the desired properties of the final formulation.

The pH of the final formulation should be adjusted such that it is suitable for topical application to the skin. There are many compounds known in the art which are suitable for adjusting the pH of the final formulations. These pH adjusters are generally acids and bases. Preferred pH adjusters for use with the present invention include sodium hydroxide and hydrochloric acid, although the choice of the pH adjuster is not critical.

The final formulation is preferably adjusted such that the final formulation has a pH in the range of about 4 to about 7, preferably from about 5 to about 7, and most preferably from about 5 to about 6. One skilled in the art will understand that a sufficient quantity of pH adjuster should be added to achieve the desired pH of the final formulation.

Pharmaceutical excipients and adjuvants such as fragrances, colorants and the like may be added. When present in the formulation, the total amount of these ingredients will be in the range of from about 0.1 to about 10% w/v of the final formulation.

Desired properties of the final formulation will depend on the intended use and desired results, and will include, but is not limited to such qualities as sudsing, concentration of the iodophor, solubility of the formulation ingredients, stability and the like. One skilled in the art will be able to adjust the amount of ingredients present to achieve the desired results, and such formulations are meant to be within the scope of the present invention.

Preferably, the iodophor formulations of the present invention are stable over the desired shelf-life of the product. Typically, for PVPI containing products, the U.S. Pharmacopeia (U.S.P) allows a 20% overage (i.e., 120%) from the label claim of available iodine and requires a minimum 85% of labelled claim of available iodine at the end of the stated product shelf-life, for example, as determined by accelerated aging (3 months/37° C.–40° C.) of the product. This translates into an allowable decrease in available iodine concentration of 35%. Therefore for 7.5% PVPI solutions, the maximum allowable limit is 9.0% PVPI and the minimum is 6.375%. Thus, stability of a 7.5% solution should be above 6.375% PVPI (or 0.6375% available iodine) during the shelf life of the product to be considered stable.

The formulations of the present invention may be prepared according to any method known in the art.

In certain embodiments of the present invention, the iodophor is dissolved in a sufficient amount of solvent or vehicle to form a solution. To this solution, the desired amount of water-soluble emollient is added and the solution mixed as necessary. The appropriate of a pH of the product may be adjusted by addition of an appropriate amount pH adjuster to the solution. Stabilizers are added to the solution if desired. If other pharmaceutical excipients such as surfactants, viscosity agents, fragrances and the like are to be included in the final formulation, they are added to the solution and mixed if necessary. The desired final volume of formulation is achieved by addition of a sufficient volume of vehicle.

The above steps may be varied in a variety of ways. For example, certain compatible ingredients may be combined together before admixture with the vehicle or vehicle/iodophor solution. Depending upon the physical state of the ingredients, certain other steps may be performed in order to achieve a suitable pharmaceutical formulation. For example, Lauramide DEA is a wax-like solid and should be melted prior to addition to the solution. Mixing should be performed where necessary in order to achieve or maintain a homogeneous solution, thus facilitating preparation of the final product.

In a preferred embodiment, the iodophor, e.g. PVPI, is dissolved in a portion of water to obtain a solution. To this solution is added the emollient and surfactants. Other adjuvants such as a fragrances are added to the solution. The pH of the formulation is adjusted by adding an appropriate amount of pH adjusting agent, e.g. NaOH, to achieve the desired pH. The formulation is then brought to the desired final volume by addition of a sufficient quantity of water. A viscosity agent may be added to adjust the viscosity final formulation to the desired range.

The choice of storage containers for formulations prepared in accordance with the present invention will depend upon the physical properties of the container material. PVPI containing formulations pose a particular storage problem because iodine has a tendency to leach into certain types of materials. Thus one should choose a container made from a material which is resistant to iodine leaching. Preferably, the formulations of the present invention will be stored in multi-application containers which contain a predetermined amount of the formulation. The volume of the formulation desired will depend on many factors, including marketing preferences, commercial uses, etc.

A multi-application unit dosage form of an antiseptic formulation prepared in accordance with the present invention includes a predetermined quantity of an antiseptic formulation prepared in accordance with the present invention, and a suitable multi-application container. Preferably, the container will be glass or plastic. Most preferably the container will be made of high density polyethylene.

Many other embodiments of the present invention will become apparent to one skilled in the art from the Examples provided below; such embodiments are intended to be within the scope of the appended claims.

DETAILED DESCRIPTION OF THE PREFERRED EMBODIMENTS

The following examples illustrate various embodiments of the present invention. They are not meant to limit the scope of the claims appended hereto in any manner whatsoever.

EXAMPLE 1

A PVP-I solution formulation containing surfactants which has been commercially used as an effective antimicrobial scrub is presented in Table I.

TABLE I

| PVPI SOLUTION WITH SURFACTANTS | |
|---|---|
| Ingredients | % w/v |
| PVPI* + Overage | 7.5 + 0.975 |
| Ammonium Nonoxynol-4 Sulfate (Trade name: Rhodapex CO-436®) | 25 |
| Lauramide DEA (Trade name: Superamide L9 ®) | 1.2 |
| Fragrance** | 0.25 |
| Sodium Hydroxide QS to pH | 5.25 |
| Purified Water qs ad | 100.0 |

*PVPI powder (10% Available Iodine)
**Used in same formulation

This formulation is prepared as follows:
1. The PVP-I is dissolved in purified water representing approximately 50% of the total batch volume.
2. To this solution is added the Ammonium Nonoxynol-4 Sulfate and mix.
3. Melt and add the Lauramide DEA. Mix to dissolve.
4. Add the fragrance.
5. Adjust pH by adding an appropriate amount of sodium hydroxide to achieve a pH of 5.25.
6. Add a sufficient quantity to achieve the desired total volume ("QSAD") with Purified Water.

This product was stable as per the FDA/USP stability criteria stated above. However, there was a significant drying effect on the skin on repeat frequent use of this product. This was considered a major complaint from users of this product.

EXAMPLES 2–6

To improve on the drying effect, modifications to the formulation in Example 1 were made as detailed in Table II. Note that the level of PVPI was reduced with varying levels of the surfactant (e.g. Ammonium Nonoxynol-4 Sulfate). A second amphoteric surfactant (Velvetex BA 35®) was included in certain formulations to reduce irritancy. Examples 3, 5, and 6 have 2.0% Lauramide DEA. A water-soluble emollient, choleth-24 and ceteth-24, was included in these examples at varying levels.

To each formulation 0.25% w/v potassium iodate was added as a stabilizer. Each formulation included a thickener (e.g. Natrosol 250 HX, Methocel E 50) to achieve the same viscosity as the formulation in Example 1. The exemplified anti-microbial PVPI solution formulations containing surfactants and a water-soluble emollient were stable. Procedures to make these are similar to that in Example 1 except as noted below.

1. The Velvetex BA 35 is added before the Lauramide DEA.
2. The Choleth-24 and Ceteth-24 is added as a melt after the Lauramide DEA.
3. The thickeners are incorporated into the batch before the addition of the PVP-I.
4. The Potassium Iodate is added to the batch after pH adjustment.

TABLE II

PVPI SOLUTION WITH SURFACTANTS AND EMOLLIENTS

| Ingredients | Ex. 2 | Ex. 3 | Ex. 4 | Ex. 5 | Ex. 6 |
|---|---|---|---|---|---|
| PVPI (10% Av. $I_2$) | 5.0 | 5.0 | 5.0 | 5.0 | 5.0 |
| Ammonium Nonoxynol-4 Sulfate | 5.0 | 5.0 | 10.0 | 10.0 | 15.0 |
| Lauramide DEA | — | 2.0 | — | 2.0 | 2.0 |
| Velvetex BA35 ® | 4.0 | — | 4.0 | — | 4.0 |
| Choleth-24 and Ceteth-24 (Solulan C-24 ®) | 0.50 | 1.0 | 0.5 | 0.5 | 1.0 |
| Natrosol 250HX ® | 0.2 | — | 0.2 | 0.2 | 0.16 |
| Methocel E50 Prem. ® | 0.5 | 1.0 | 0.5 | 0.5 | — |
| Potassium Iodate | 0.25 | 0.25 | 0.25 | 0.25 | 0.25 |
| NaOH/HCl qs to pH | (5.25) | (5.25) | (5.25) | (5.25) | (5.25) |
| Purified water qs ad | 100 | 100 | 100 | 100 | 100 |

To evaluate the mildness and other attributes between the formulation with an emollient (Examples 2–6) and one without (Example 1) a survey was conducted among 24 volunteers in a hand-wash test where the sample formulations were blinded. Each volunteer was instructed to wash 7–14 times per day. The six lots were not distributed in the same order to all participants. Changing the order of distribution prevented opinions from flowing from one participant to another (18 participants completed the test).

Each participant was asked to rate the different formulations in terms of:
1. Kindness to Hands
2. Sudsing/Foaming Action
3. Antiseptic/Cleansing Effect
4. Fragrance
5. Viscosity
6. Overall Each of the above attributes was assigned a weighing factor as follows:

| | |
|---|---|
| Excellent = | +4 |
| Good = | +2 |
| Fair = | +1 |
| Poor = | −1 |

SUMMARY OF RESULTS

The weighted results ranged from a high of 200 points for Example 1 to a low of 68 for Example 2.

| | Weighted Numbers Example | | | | | |
|---|---|---|---|---|---|---|
| | Example | | | | | |
| Test Attribute | 2 | 4 | 6 | 5 | 3 | 1 |
| Kindness to Hands | 14 | 26 | 20 | 14 | 14 | 31 |
| Sudsing/Foaming Action | 3 | 27 | 31 | 22 | 18 | 34 |
| Antiseptic/Cleansing Effect | 29 | 31 | 35 | 29 | 25 | 36 |
| Fragrance | 3 | 0 | 10 | 10 | 15 | 28 |
| Viscosity | 15 | 28 | 30 | 25 | 27 | 36 |
| Overall | 4 | 19 | 28 | 18 | 13 | 35 |
| Total | 68 | 131 | 154 | 118 | 112 | 200 | i. Example 1 scored the highest number of weighted points in all categories.

ii. Example 6 was the second most liked formulation with a rating of 154 points. Example 6 came in only one point below Example 1 in Antiseptic/Cleansing Effect and three points below Example 1 in Sudsing/Foaming Action.

iii. Lastly, Example 2 rated poorly in all areas, except Antiseptic/Cleansing Effect, but Example 2 still resulted in the lowest score of 68.

These findings indicated that reduction in the overall detergent concentration, inclusion of a water-soluble emollient (at up to 1% concentration) did not provide the desired characteristics and that the formulation without the water-soluble emollient was superior.

EXAMPLE 7

A second emollient (Softigen 767®) was also evaluated. The formulation is given in Table III. The concentration of 1–2% Softigen 767® was recommended by the manufacturer.

TABLE III

PVPI SOLUTION WITH SURFACTANT AND EMOLLIENT

| Ingredients | % w/v |
|---|---|
| PVPI (10% Av. Iodine) | 5.0 |
| Ammonium Nonoxynol-4 Sulfate | 5.0 |
| Lauramide DEA | 1.2 |
| Softigen 767 ® | 2.0 |
| Natrosol 250 HX ® | 0.3 |
| Potassium Iodate | 0.15 |
| Sodium Hydroxide (QS pH) | 5.0 |
| Purified Water qs ad | 100.0 |

The method of preparation is the same as in Examples 2–7. The Softigen 767® (which is a liquid) is added after the Lauramide DEA. This formulation was compared against the formulation in Example 6 and was found to be comparable but not as desirable as the formulation in Example 1.

As these emollients were not expected to be retained on the skin these findings were not entirely surprising.

EXAMPLES 8–11

Further studies were conducted with formulation similar to the preferred formula (Example 6) but with increased concentration of emollients and a variety of emollients. These formulations are presented in Table IV below. It should be noted that the concentrations of emollients used were higher than that recommended by the manufacturer.

TABLE IV

PVPI SOLUTION WITH SURFACTANT AND EMOLLIENTS (% W/V)

| Ingredient | Ex. 8 | Ex. 9 | Ex. 10 | Ex. 11 |
|---|---|---|---|---|
| PVPI + Overage | 7.5 + 1.35 | 7.5 + 1.35 | 7.5 + 1.35 | 7.5 + 1.35 |
| Ammonium Nonoxynol-4 Sulfate | 18.0 | 18.0 | 18.0 | 18.0 |
| Lauramide DEA | 1.2 | 1.2 | 1.2 | 1.2 |
| Glucam E20 ® | — | — | 5.0 | — |
| Solulan C-24 ® | — | 3.0 | — | — |
| Softigen 767 ® | 4.0 | — | — | — |
| Aloe Powder | — | — | — | 0.5 |
| NaOH | To pH 5.25 | To pH 5.25 | To pH 5.25 | To pH 5.25 |
| P. water qs ad 100 | 100 | 100 | 100 | 100 |

It should be noted that all four formulations contained an 18% PVPI overage and 18% Ammonium Nonoxynol-4 Sulfate while Example 1 contains 13% PVPI overage and 25% Ammonium Nonoxynol-4 Sulfate. Each of the four formulations contains a different emollients. It was hoped that the reduced surfactant concentration would help reduce the defatting effect of the surfactant on the skin.

EXAMPLE 8

The emollient used in this formulation is Softigen 767®. Softigen 767® is Polyethylene-6 Glycerol-Caprylate/Caprate. The manufacturer recommends using 1–2% Softigen 767®.

EXAMPLE 9

The emollient used in this formulation is Solulan C-24® (CFTA name Choleth-24 and Ceteth-24). The manufacturer recommends using 1–2% in combination with other fats for topical use.

EXAMPLE 10

The emollient used in this formulation is Glucam E 20® (CFTA Adopted name: Methyl Gluceth –20). It is the 20 mole ethoxylate of methyl glucose.

EXAMPLE 11

The emollient used in this formulation was Aloe powder.

The four batches were placed on stability in 8 oz. HDPE bottles with Seaquist Caps. The stability data for each formulation is present in Table V, VI, VII, VIII respectively.

These formulations (Examples 8, 9, 10, 11) and the formulation in Example 1 were tested in the clinic for their emolliency as follows:

A randomized double-blind comparative study evaluating the mildness/irritancy potential of these four formulations compared to the PVPI solution with surfactant (Example 1) was conducted. The design of this protocol was a double-blind parallel group study where subjects were randomized to one of four treatment groups. Each of the groups tested a different formulation of PVPI solution with surfactants and emollient (emollient #1: Example #8, emollient #2: Example 9, emollient #3: Example #10, emollient #4: Example #11).

In addition, each subject was further randomized as to which hand was washed with the PVPI solution Scrub with detergent (Example 1) and which hand was washed with the PVPI solution with surfactant containing an emollient.

It was concluded that the test formulations and the control formulations are equally disruptive to the stratum corneum therefore clinically there is no difference between the formulations. The subjective preference test indicated a trend toward emollient #2: Example #9. As can be seen even with the emollient concentration being increased 300% for Solulan C-24® (Example 6 to Example 9) and 200% for Softigen 767® (Example 7 to Example 8) the formulation were still no different than the formulation in Example 1.

This finding was not surprising as the emollients were most likely being washed off the skin. It should be noted however that all the formulations met the USP/FDA stability criteria.

EXAMPLE 12

Based on the clinical findings and stability data, a formulation was made where the PVPI overage was reduced to 5%, the concentration of the emollient from Example #9 (Solulan C-24®) was increased 66% (from 3% to 5% w/v). This formulation is presented in Table IX.

In Table X is presented the stability data for the formulation in Example 12. The data shows that there is a dramatic decrease in the % Available Iodine found and this can be attributed to the higher concentration of the emollient (5% Solulan C-24®) used in this formulation. Although for the time period studied the formulation is stable as per USP/FDA criteria, the % Av. Iodine is approaching the lower limit of the allowable specification as discussed earlier.

EXAMPLE 13

Based on the above considerations, a formulation was made where the PVPI overage was 13 (Table XI) the same as in Example 1. The stability data for this formulation was well within specifications and is presented in Table XII.

TABLE V

PVPI SOLUTION WITH SURFACTANTS AND EMOLLIENT (4% SOFTIGEN 767 ®)
Example #8, Packaging: 8 oz. HDPE Bottle

| SPECIFICATIONS Storage Conditions & Test Time | % Av Iodine 0.75 0.64–0.90 | pH 1.5–6.5 | Appearance RBS* |
|---|---|---|---|
| Initial RT | 0.878 | 5.0 | RBS |
| 2 week | 0.863 | 4.50 | RBS |
| 3 months | 0.873 | 4.44 | RBS |
| 6 months | 0.858 | 4.40 | RBS |
| 37° C./80% RH | | | |
| 1 week | 0.873 | 4.28 | RBS |
| 2 weeks | 0.870 | 4.26 | RBS |
| 3 weeks | 0.861 | 4.10 | RBS |
| 37° C./80% RH | | | |
| 1 month | 0.835 | 4.07 | RBS |
| 2 months | 0.829 | 4.03 | RBS |
| 3 months | 0.834 | 4.00 | RBS |

*RBS = Reddish-brown solution.

TABLE VI

PVPI SOLUTION WITH SURFACTANTS AND EMOLLIENT (3% SOLULAN C-24 ®)
Example #9, Packaging: 8 oz. HDPE Bottle

| SPECIFICATIONS Storage Conditions & Test Time | % Av Iodine 0.75 0.64–0.90 | pH 1.5–6.5 | Appearance RBS* |
|---|---|---|---|
| Initial | 0.833 | 4.88 | RBS |
| RT |  |  |  |
| 2 week | 0.830 | 4.42 | RBS |
| 3 months | 0.834 | 4.37 | RBS |
| 6 months | 0.838 | 4.34 | RBS |
| 37° C./80% RH |  |  |  |
| 1 week | 0.815 | 4.79 | RBS |
| 2 weeks | 0.805 | 4.57 | RBS |
| 3 weeks | 0.783 | 4.31 | RBS |
| 37° C./80% RH |  |  |  |
| 1 month | 0.769 | 4.30 | RBS |
| 2 months | 0.771 | 4.18 | RBS |
| 3 months | 0.771 | 4.11 | RBS |

*RBS = Reddish-brown solution.

TABLE VII

PVPI SOLUTION WITH SURFACTANTS AND EMOLLIENT (5% GLUCAM E-20 ®)
Example #10, Packaging: 8 oz. HDPE Bottle

| SPECIFICATIONS Storage Conditions & Test Time | % Av Iodine 0.75 0.64–0.90 | pH 1.5–6.5 | Appearance RBS* |
|---|---|---|---|
| Initial | 0.843 | 5.01 | RBS |
| RT |  |  |  |
| 2 week | 0.840 | 4.47 | RBS |
| 3 months | 0.844 | 4.44 | RBS |
| 6 months | 0.827 | 4.39 | RBS |
| 37° C./80% RH |  |  |  |
| 1 week | 0.835 | 4.44 | RBS |
| 2 weeks | 0.832 | 4.39 | RBS |
| 3 weeks | 0.831 | 4.32 | RBS |
| 37° C./80% RH |  |  |  |
| 1 month | 0.820 | 4.30 | RBS |
| 2 months | 0.816 | 4.25 | RBS |
| 3 months | 0.821 | 4.19 | RBS |

*RBS = Reddish-brown solution.

TABLE VIII

PVPI SOLUTION WITH SURFACTANTS AND EMOLLIENT (0.5% ALOE POWDER)
Example #11, Packaging: 8 oz. HDPE Bottle

| SPECIFICATIONS Storage Conditions & Test Time | % Av Iodine 0.75 0.64–0.90 | pH 1.5–6.5 | Appearance RBS* |
|---|---|---|---|
| Initial | 0.881 | 5.18 | RBS |
| RT |  |  |  |
| 2 week | 0.863 | 4.71 | RBS |
| 3 months | 0.884 | 4.66 | RBS |
| 6 months | 0.858 | 4.62 | RBS |
| 37° C./80% RH |  |  |  |
| 1 week | 0.865 | 4.59 | RBS |
| 2 weeks | 0.858 | 4.47 | RBS |
| 3 weeks | 0.854 | 4.38 | RBS |
| 37° C./80% RH |  |  |  |
| 1 month | 0.840 | 4.37 | RBS |
| 2 months | 0.822 | 4.34 | RBS |
| 3 months | 0.821 | 4.31 | RBS |

*RBS = Reddish-brown solution.

TABLE IX

PVPI SOLUTION WITH SURFACTANTS AND EMOLLIENT (SOLULAN C-24 ®)

| Ingredient | Example 12 % w/v |
|---|---|
| PVPI + Overage | 8.475 |
| Alipal CO 436 ® | 15.0 |
| Superamide L9 ® | 1.2 |
| Solulan C-24 ® | 6.0 |
| Sodium Hydroxide to pH | (5.25) |
| Purified Water qs ad | 100.0 |

TABLE X

PVPI SOLUTION WITH SURFACTANTS AND EMOLLIENT (5% SOLULAN C-24 ®) (5% PVPI OVERAGE)
Example #12, Packaging: 240 CC HDPE Bottle

| SPECIFICATIONS Storage Conditions & Test Time | % Av Iodine 0.75 0.64–0.90 | pH 1.5–6.5 | Appearance RBS* |
|---|---|---|---|
| Initial | 0.755 | 4.64 | RBS |
| RT |  |  |  |
| 2 week | 0.713 | 3.8 | RBS |
| 3 months | 0.682 | 4.06 | RBS |
| 6 months | 0.658 | 4.80 | RBS |
| 37° C./80% RH |  |  |  |
| 1 week | 0.67 | 4.0 | RBS |
| 2 weeks | 0.66 | 4.1 | RBS |
| 3 weeks | 0.65 | 4.1 | RBS |

*RBS = Reddish-brown solution.

TABLE XI

PVPI SOLUTION WITH SURFACTANTS AND EMOLLIENT (5% SOLULAN C-24 ®) 13% PVPI OVERAGE

| Ingredients | Example 13 % w/v |
|---|---|
| PVPI + Overage | 7.5 + 0.975 |
| Alipal CO 436 ® | 15.0 |
| Superamide L9 ® | 1.2 |
| Solulan C-24 ® | 5.0 |

TABLE XI-continued

PVPI SOLUTION WITH SURFACTANTS AND
EMOLLIENT (5% SOLULAN C-24 ®)
13% PVPI OVERAGE

| Ingredients | Example 13 % w/v |
| --- | --- |
| Sodium Hydroxide to pH | (5.25) |
| Purified Water qs ad | 100.0 |

TABLE XII

PVPI SOLUTION WITH SURFACTANTS AND EMOLLIENT
(5% SOLULAN C-24 ®) 13% PVPI OVERAGE
STABILITY PERFORMANCE DATA
Example #13, Packaging: 8 oz. HDPE Bottle

| SPECIFICATIONS Storage Conditions & Testing Time | % Av Iodine (Label 0.75% (0.64–0.90 w/v) | % Loss | pH 1.5–6.5 | Appearance RBS* |
| --- | --- | --- | --- | --- |
| Initial RT | 0.755 | — | 3.61 | RBS |
| 3 months 37° C./80% RH | 0.863 | (3%) | 3.76 | RBS |
| 1 month | 0.715 | (5%) | 3.82 | RBS |
| 2 months | 0.683 | (9%) | 3.94 | RBS |
| 3 months | 0.668 | (11%) | 3.96 | RBS |

RBS = Reddish-brown solution.

The formulation from Example #13 which had met the FDA/USP stability criteria was then tested in the clinics in two separate studies as follows:

A. Randomized Double Blind Comparative Study

A randomized double-blind comparative study was conducted to evaluate the mildness/irritancy potential of test formulations of PVPI solution with surfactant and emollient (Example #13) compared to the PVPI solution with surfactant (Example 1).

The objective of this randomized, double-blind study was to evaluate and compare the mildness/irritancy potential of the formulation with the emollient (Example #13) when used repeatedly in an aggressive handwashing.

It was found that the primary endpoint, transepidermal water loss (TWL), indicated there was a statistically significant increase in evaporation water loss after completing this handwash protocol for both the hand washed with an emollient containing formula (Example #13) and the hand washed with a formulation without the emollient (Example 1). However, it was surprising that there was a significantly lower TWL for the test formulation with the emollient. Clinically, increased TWL means the stratum corneum is being disturbed which leads to erythema and dryness. Because there was a difference between the test and control formulations the stratum corneum was disturbed to a greater extent by the formulation without the emollient (Example 1) than by the formulation with emollient (Example 13). This was a surprising discovery.

We were further surprised to find that there was a significant difference in the average final erythema score between the hand washed with the formulation containing emollient and control hands. The hand washed with the formulation containing emollient showing less redness. There was no difference in the average final dryness score between the hand washed with the formulation containing emollient and the control hand. Over the course of the study the raters did not score marked or severe erythema for either the hand washed with the formulation containing emollient or control hand.

Also a surprising finding was a significant preference by the expert raters at time of final evaluation for the hands washed with the formulation containing emollient (p<0.0001). However, the subjects did not show a clear preference. Clinically, the expert raters' preference for the hands washed with the formulation containing emollient is of value since it is supported by the TWL and erythema findings.

Thus, on the basis of TWL, erythema, and expert ratings, the PVP-I solution with surfactant and an emollient was a less irritating formulation than the formulation without the emollient.

B. "Use" Preference Study

Based on these surprising findings and to further study this phenomenon that when a critical minimum concentration of the emollient is reached (5%, as for Solulan C-24® in Example #13) the emollient was surprisingly found to be effective even on washing the hands. A possible theory is that at a minimum critical concentration the emollient binds to the skin and so is not washed away by the rinsing process.

This application where a water soluble emollient incorporated into an aqueous PVPI containing formulation (with surfactant) at concentrations well above the concentration generally used by someone familiar in the art is novel.

Further, a study was conducted to evaluate the preference between the formulation with emollient (Example #13) and a formulation without emollient (Example #1) when used over a two week period by medical personnel who regularly used the commercial PVPI Scrub product 6–10 times a day.

The study concluded that:

Overall satisfaction with the test product containing emollient showed 66% of the panelists rating it as "Excellent" or "Good".

Top three "Attributes" were: "Feels soft/smooth/softened skin"; "Cleans well"; and "Less dryness/cracking."

The pre-test comments regarding "Drying" and "Chapping" were greatly reduced.

82% preferred the test product to their normal product; and the biggest reason given related to improvement in chapping/dryness.

As the above results indicate, test product fared very well in this use study. It appears that the addition of emollient at a critical minimum concentration to PVPI solution with surfactant had a definite and positive beneficial effect.

Antimicrobial Efficacy

A study was conducted to compare the antimicrobial efficacy in-vitro of the formulation in Example #13 (with emollient) and the formulation in Example #1 (without emollient) as follows:

In-vitro Killing Time Versus Vegetative Organisms.

Both formulations were tested undiluted. Killing times were determined versus *Pseudomonas aeruginosa*, *Escherichia coli*, *Staphylococcus aureus*, *Candida albicans*, *Aspergillus niger*, *Pseudomonas cepacia*, *Proteus mirabilis*, and *Gardnerella vaginalis*. A negative control (sterile distilled water) was also tested. The data is summarized in Tables XIII, XIV, XV.

In-Vitro Killing Time Versus Spores of Bacillus pumilus ($D_{10}$ Value).

Both formulations were tested full strength and spore counts were made at several time points up to 30 minutes as well as at 1, 3, 6, and 24 hours. A negative control (sterile distilled water) was also examined.

Results

Both formulations had similar antimicrobial activity against vegetative microorganisms. Numerically, the formulation with emollients displayed slightly better killing activity against Candida albicans. In this experiment, neither formulation was effective against Aspergillus niger. Both of the formulations effective in reducing Bacillus pumilus spores by 3 log units after 24 hours. The D10 values were 7.4 hours for the formulation with Emollients and 5.6 hours for the formulation without emollient.

Animal Skin Irritation Studies

To ensure that the addition of the emollient had no significant effect on animal skin irritation, a comparative dermal irritation study was conducted with the formulation in Example #13 (with emollient) and Example #1 (without emollient) as follows.

In this study the irritant effects of the formulation with emollient (Example #13) were compared with the formulation which did not contain emollient (Example #1), using a standard rabbit decal irritation model. In brief, the two formulations were applied undiluted to the skin of 3 male and 3 female New Zealand white rabbits. A dose of 0.5 of each material was applied to separate intact and abraded sites of each rabbit. The test materials were held in contact with the skin by a semiocclusive bandage during a 24 hour exposure period and were evaluated for irritation and skin discoloration at approximately 25 hours, 72 hours, 7, 10, and 14 days after the beginning of the exposure period (i.e., 1 hour, 48 hours, 6, 9 and 13 days after removal of the semiocclusive bandage). The 2 formulations were coded so that the testing laboratory did not know the identity of the formulations. Animals treated topically with saline (negative control) or 10% sodium lauryl sulfate (positive control) were also evaluated to ensure the integrity of the experiment.

Results

The average irritation scores for intact skin, abraded skin, and the combination of the two (primary irritation index [PII]) are given below:

|  | Intact | Abraded | PII |
|---|---|---|---|
| Formulation in Example #1 | 4.17 | 4.58 | 4.38 |
| Formulation in Example #13 (with emollient) | 2.83 | 3.25 | 3.04 |

Conclusion: Formulation with emollient was slightly less irritating to rabbit skin than the formulation without emollient.

Neither of these products would be considered to be a primary dermal irritant according to the guidelines of the US Consumer Product Safety Commission (i.e., both had primary irritations indices of <5).

TABLE XIII

IN-VITRO ANTIMICROBIAL EFFICACY STUDY FORMULATION WITH EMOLLIENT (EXAMPLE #13)

| Inoculum: ATCC: Lab. No: R2055 | Pseudo- monas aeruginosa ATCC 9027 | Escher- ichia coli ATCC 8739 | Staphy- lococcus aureus ATCC 6538 | Candida albicans ATCC 10231 |
|---|---|---|---|---|
| Time | | | | |
| Initial | $2.3 \times 10^5$ | $1.8 \times 10^5$ | $1.4 \times 10^5$ | $1.1 \times 10^5$ |
| 30 Seconds | <10 | <10 | <10 | $2.1 \times 10^4$ |
| 60 Seconds | <10 | <10 | <10 | $8.9 \times 10^3$ |
| 3 Minutes | <10 | <10 | <10 | $1.5 \times 10^2$ |
| 5 Minutes | <10 | <10 | <10 | <10 |
| 10 Minutes | <10 | <10 | <10 | <10 |
| 15 Minutes | <10 | <10 | <10 | <10 |
| 30 Minutes | <10 | <10 | <10 | <10 |

| Inoculum: ATCC: Lab. No: R2055 | Asper- gillus niger ATCC 16404 | Pseudo- monas cepacia ATCC 25416 | Proteus Mirabili ATCC 29245 | Gardner- ella vaginalis ATCC 14018 |
|---|---|---|---|---|
| Time | | | | |
| Initial | $2.2 \times 10^5$ | $3.8 \times 10^5$ | $4.1 \times 10^5$ | $2.7 \times 10^5$ |
| 30 Seconds | $2.1 \times 10^5$ | <10 | <10 | <10 |
| 60 Seconds | $2.3 \times 10^5$ | <10 | <10 | <10 |
| 3 Minutes | $2.0 \times 10^5$ | <10 | <10 | <10 |
| 5 Minutes | $1.8 \times 10^5$ | <10 | <10 | <10 |
| 10 Minutes | $1.6 \times 10^5$ | <10 | <10 | <10 |
| 15 Minutes | $1.5 \times 10^5$ | <10 | <10 | <10 |
| 30 Minutes | $1.2 \times 10^5$ | <10 | <10 | <10 |

TABLE XIV

IN-VITRO ANTIMICROBIAL EFFICACY STUDY FORMULATION WITHOUT EMOLLIENT (EXAMPLE #1)

| Inoculum: ATCC: Lab. No: R2056 | Pseudo- monas aeruginosa ATCC 9027 | Escher- ichia coli ATCC 8739 | Staphy- lococcus aureus ATCC 6538 | Candida albicans ATCC 10231 |
|---|---|---|---|---|
| Time | | | | |
| Initial | $3.4 \times 10^5$ | $2.7 \times 10^5$ | $1.9 \times 10^5$ | $1.9 \times 10^5$ |
| 30 Seconds | <10 | <10 | <10 | $8.4 \times 10^4$ |
| 60 Seconds | <10 | <10 | <10 | $8.2 \times 10^3$ |
| 3 Minutes | <10 | <10 | <10 | $1.4 \times 10^3$ |
| 5 Minutes | <10 | <10 | <10 | $6.7 \times 10^2$ |
| 10 Minutes | <10 | <10 | <10 | <10 |
| 15 Minutes | <10 | <10 | <10 | <10 |
| 30 Minutes | <10 | <10 | <10 | <10 |

| Inoculum: ATCC: Lab. No: R2056 | Asper- gillus niger ATCC 16404 | Pseudo- monas cepacia ATCC 25416 | Proteus Mirabilis ATCC 29245 | Gardner- ella vaginalis ATCC 14018 |
|---|---|---|---|---|
| Time | | | | |
| Initial | $2.6 \times 10^5$ | $1.9 \times 10^5$ | $2.6 \times 10^5$ | $2.2 \times 10^5$ |
| 30 Seconds | $2.4 \times 10^5$ | <10 | <10 | <10 |
| 60 Seconds | $2.3 \times 10^5$ | <10 | <10 | <10 |
| 3 Minutes | $2.1 \times 10^5$ | <10 | <10 | <10 |
| 5 Minutes | $1.8 \times 10^5$ | <10 | <10 | <10 |
| 10 Minutes | $1.7 \times 10^5$ | <10 | <10 | <10 |
| 15 Minutes | $1.6 \times 10^5$ | <10 | <10 | <10 |
| 30 Minutes | $1.4 \times 10^5$ | <10 | <10 | <10 |

TABLE XV

IN-VITRO ANTIMICROBIAL STUDY
NEGATIVE CONTROL (STERILE DI WATER)

| Inoculum:<br>ATCC:<br>Lab. No:<br>R2055 | Pseudo-<br>monas<br>aeruginosa<br>ATCC 9027 | Escher-<br>ichia<br>coli<br>ATCC<br>8739 | Staphy-<br>lococcus<br>aureus<br>ATCC<br>6538 | Candida<br>albicans<br>ATCC<br>10231 |
|---|---|---|---|---|
| Time | | | | |
| Initial | $7.8 \times 10^5$ | $5.9 \times 10^5$ | $8.4 \times 10^5$ | $1.4 \times 10^5$ |
| 30 Seconds | $7.1 \times 10^5$ | $4.3 \times 10^5$ | $7.5 \times 10^5$ | $1.9 \times 10^5$ |
| 60 Seconds | $8.9 \times 10^5$ | $6.2 \times 10^5$ | $7.1 \times 10^5$ | $2.7 \times 10^5$ |
| 3 Minutes | $9.3 \times 10^5$ | $7.1 \times 10^5$ | $8.9 \times 10^5$ | $2.6 \times 10^5$ |
| 5 Minutes | $7.4 \times 10^5$ | $3.8 \times 10^5$ | $9.5 \times 10^5$ | $3.1 \times 10^5$ |
| 10 Minutes | $6.2 \times 10^5$ | $4.9 \times 10^5$ | $7.3 \times 10^5$ | $1.4 \times 10^5$ |
| 15 Minutes | $6.9 \times 10^5$ | $5.2 \times 10^5$ | $7.10 \times 10^5$ | $1.7 \times 10^5$ |
| 30 Minutes | $8.3 \times 10^5$ | $5.5 \times 10^5$ | $8.8 \times 10^5$ | $1.9 \times 10^5$ |

| Inoculum:<br>ATCC:<br>Lab No:<br>R2055 | Asper-<br>gillus<br>niger ATCC<br>16404 | Pseudo-<br>monas<br>cepacia<br>ATCC<br>25416 | Proteus<br>Mirabili<br>s ATCC<br>29245 | Gardner-<br>ella<br>vaginalis<br>ATCC<br>14018 |
|---|---|---|---|---|
| Time | | | | |
| Initial | $3.9 \times 10^5$ | $1.7 \times 10^5$ | $9.4 \times 10^5$ | $4.3 \times 10^5$ |
| 30 Seconds | $2.1 \times 10^5$ | $1.3 \times 10^5$ | $9.2 \times 10^5$ | $4.1 \times 10^5$ |
| 60 Seconds | $2.5 \times 10^5$ | $1.1 \times 10^5$ | $8.9 \times 10^5$ | $4.4 \times 10^5$ |
| 3 Minutes | $2.8 \times 10^5$ | $1.2 \times 10^5$ | $9.5 \times 10^5$ | $5.2 \times 10^5$ |
| 5 Minutes | $1.6 \times 10^5$ | $1.9 \times 10^5$ | $8.7 \times 10^5$ | $3.9 \times 10^5$ |
| 10 Minutes | $2.3 \times 10^5$ | $1.1 \times 10^5$ | $8.3 \times 10^5$ | $3.6 \times 10^5$ |
| 15 Minutes | $2.2 \times 10^5$ | $1.0 \times 10^5$ | $9.1 \times 10^5$ | $4.7 \times 10^5$ |
| 30 Minutes | $2.8 \times 10^5$ | $1.3 \times 10^5$ | $8.3 \times 10^5$ | $4.1 \times 10^5$ |

The examples provided above are not meant to be exclusive. Many other variations of the present invention would be obvious to those skilled in the art, and are contemplated to be within the scope of the appended claims.

What is claimed is:

1. A topical formulation comprising:
   an anti-microbially effective amount of povidone iodine; and from 2% to about 30% of a water-soluble emollient comprising from about 1 to about 99% ethoxylated higher aliphatic alcohol and from about 1 to about 99% ethoxylated cholesterol derivative.

2. The topical formulation of claim 1, comprising from about 2 to about 20% povidone iodine.

3. The topical formulation of claim 1, comprising about 7.5% w/v of said povidone iodine; from about 2 to about 20% surfactant; and at least 5% to about 30% w/v water soluble emollient.

4. The topical formulation of claim 3, having a pH of from about 1.5 to about 6.5.

5. The topical formulation of claim 2, wherein said water-soluble emollient comprises from about 3 to about 5% of the formulation by weight.

6. The topical formulation of claim 1, wherein said povidone iodine is included in an amount which provides from about 1 to about 30% available iodine.

7. The topical formulation of claim 1, further comprising from about 0.5% to about 30% of a surfactant selected from the group consisting of ethoxylated higher aliphatic alcohol derivatives, ethanol amines reacted with fatty acids, and mixtures thereof.

8. The topical formulation of claim 1, further comprising a stabilizer selected from the group consisting of iodine, an iodine salt or a combination thereof.

9. The topical formulation of claim 4, further comprising a pH adjuster.

10. The topical formulation of claim 1, further comprising a viscosity agent.

11. The topical formulation of claim 1, further comprising a stabilizer comprising potassium iodate.

12. The topical formulation of claim 1, further comprising from about 0.1 to about 10% w/v of a fragrance.

13. The topical formulation of claim 1 which is contained within a high density polyethylene container.

14. A method for preparing a topical formulation comprising the steps of:
   incorporating
      from about 1 to about 99% ethoxylated higher aliphatic alcohol and from about 1 to about 99% ethoxylated cholesterol derivative or into a solution comprising an anti-microbially effective amount of povidone iodine and greater than 2 to about 30% of a water-soluble emollient.

15. The method of claim 14, further comprising adjusting the pH of said formulation to from about 1.5 to about 6.5.

16. A method of treating human skin, comprising the steps of: applying to human skin a topical formulation comprising an anti-microbially effective amount of an iodophor; and greater than 2% of a water-soluble emollient comprising
   from about 1 to about 99% ethoxylated higher aliphatic alcohol and from about 1 to about 99% ethoxylated cholesterol derivative.

17. The method of claim 16, wherein said iodophor is povidone iodine in an amount which provides from about 1 to about 30% available iodine in said formulation, and said emollient comprises an anti-microbially effective amount of povidone iodine and greater than 2 to about 30% of a water-soluble emollient comprising from about 1 to about 99% of an ethoxylated higher aliphatic alcohol and from about 1 to about 99% of an ethoxylated cholesterol derivative.

18. In a topical formulation which contains an antimicrobially effective amount of povidone iodine, the improvement comprising incorporating into said formulation greater than 2% of a water-soluble emollient comprising
   from about 1 to about 99% ethoxylated higher aliphatic alcohol and from about 1 to about 99% ethoxylated cholesterol derivative.

19. The formulation of claim 18, wherein said water-soluble emollient is a combination of from about 2 to about 30% of a water-soluble emollient comprising from about 1 to about 99% of an ethoxylated higher aliphatic alcohol and from about 1 to about 99% of an ethoxylated cholesterol derivative.

* * * * *